United States Patent
Fujiwara et al.

(10) Patent No.: US 9,918,685 B2
(45) Date of Patent: Mar. 20, 2018

(54) MEDICAL IMAGE PROCESSING APPARATUS AND METHOD FOR MEDICAL IMAGE PROCESSING

(71) Applicant: Toshiba Medical Systems Corporation, Otawara-shi (JP)

(72) Inventors: Megumu Fujiwara, Sakura (JP); Masahiro Ozaki, Otawara (JP); Yasuko Fujisawa, Nasushiobara (JP); Manabu Hiraoka, Nasushiobara (JP); Tatsuo Maeda, Nasushiobara (JP); Tatsuya Kimoto, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 129 days.

(21) Appl. No.: 14/827,638

(22) Filed: Aug. 17, 2015

(65) Prior Publication Data

US 2016/0055647 A1  Feb. 25, 2016

(30) Foreign Application Priority Data

Aug. 19, 2014 (JP) .................................. 2014-166686

(51) Int. Cl.
*A61B 5/11* (2006.01)
*A61B 6/03* (2006.01)
(Continued)

(52) U.S. Cl.
CPC .............. *A61B 6/486* (2013.01); *A61B 5/103* (2013.01); *A61B 5/1121* (2013.01);
(Continued)

(58) Field of Classification Search
CPC ......... A61B 5/00; A61B 5/0033; A61B 5/004; A61B 5/0059; A61B 5/0073; A61B 5/0082; A61B 5/103; A61B 5/11; A61B 5/1121; A61B 5/1122; A61B 5/1126; A61B 5/1128; A61B 5/45; A61B 5/4528; A61B 5/4538; A61B 5/458; A61B 5/4585; A61B 5/459;
(Continued)

(56) References Cited

U.S. PATENT DOCUMENTS 5,099,859 A * 3/1992 Bell ..................... A61B 5/1121
348/E5.086
6,560,476 B1 * 5/2003 Pelletier ................ G06T 7/0012
382/130
(Continued)

FOREIGN PATENT DOCUMENTS

JP  2013-172816  9/2013
JP  2013-172820  9/2013

*Primary Examiner* — Anastasia Midkiff
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry obtains a plurality of medical image groups in which respective motions of a part inside a subject have been photographed in time series and executes certain processing on the acquired medical image groups. The processing circuitry analyzes the motions in the respective medical image groups. The processing circuitry generates a medical image in which the motions in the respective medical image groups substantially match with each other based on the analyzed motions.

11 Claims, 13 Drawing Sheets

(51) Int. Cl.
*G06T 7/20* (2017.01)
*A61B 6/00* (2006.01)
*A61B 5/00* (2006.01)
*A61B 5/103* (2006.01)
*G06T 7/00* (2017.01)
*G06T 7/215* (2017.01)
*G06T 7/38* (2017.01)
*G06T 7/73* (2017.01)
*G06T 7/246* (2017.01)

(52) U.S. Cl.
CPC .......... *A61B 5/1122* (2013.01); *A61B 5/1128* (2013.01); *A61B 5/459* (2013.01); *A61B 5/4528* (2013.01); *A61B 6/032* (2013.01); *A61B 6/5205* (2013.01); *A61B 6/5217* (2013.01); *A61B 6/5235* (2013.01); *G06T 7/0016* (2013.01); *G06T 7/215* (2017.01); *G06T 7/38* (2017.01); *G06T 7/97* (2017.01); *A61B 6/463* (2013.01); *A61B 6/505* (2013.01); *G01N 2800/10* (2013.01); *G01N 2800/105* (2013.01); *G06T 7/246* (2017.01); *G06T 7/73* (2017.01); *G06T 2207/10016* (2013.01); *G06T 2207/10081* (2013.01); *G06T 2207/20044* (2013.01); *G06T 2207/30008* (2013.01)

(58) Field of Classification Search
CPC ....... A61B 5/4595; A61B 5/4542; A61B 5/70; A61B 6/00; A61B 6/02; A61B 6/03; A61B 6/46; A61B 6/461; A61B 6/463; A61B 6/48; A61B 6/486; A61B 6/50; A61B 6/525; A61B 6/52; A61B 6/5211; A61B 6/5217; A61B 6/5229; A61B 6/5235; A61B 2576/00; A61B 2576/02; G06T 3/00; G06T 3/0006; G06T 3/0068; G06T 3/0075; G06T 3/20; G06T 3/60; G06T 7/00; G06T 7/0012; G06T 7/0014; G06T 7/0016; G06T 7/20; G06T 7/215; G06T 7/246; G06T 7/248; G06T 7/251; G06T 7/30; G06T 7/33; G06T 7/337; G06T 7/344; G06T 7/38; G06T 7/97; G06T 2210/41; G06T 2207/00; G06T 2207/10; G06T 2207/10016; G06T 2207/10072; G06T 2207/10076; G06T 2207/10081; G06T 2207/10088; G06T 2207/10116; G06T 2207/20; G06T 2207/20036; G06T 2207/20044; G06T 2207/20092; G06T 2207/20104; G06T 2207/20108; G06T 2207/20212; G06T 2207/20228; G06T 2207/30; G06T 2207/30004; G06T 2207/30008; G06T 2211/00; G06T 2211/40; G06F 19/30; G06F 19/321; G06F 19/34; G06F 19/3437; H05G 1/00; H05G 1/60; H05G 1/62; G01N 2800/00; G01N 2800/10; G01N 2800/101; G01N 2800/102; G01N 2800/105

See application file for complete search history.

(56) References Cited

U.S. PATENT DOCUMENTS

2008/0069418 A1\* 3/2008 Bystrov ................. G06T 13/20
 382/131
2013/0223703 A1\* 8/2013 Fujisawa ............... G06F 19/321
 382/128

\* cited by examiner

FIG.4B
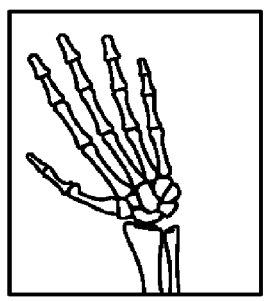 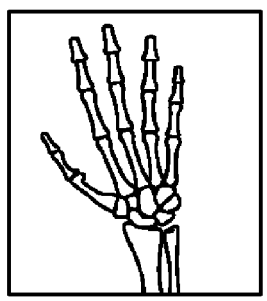 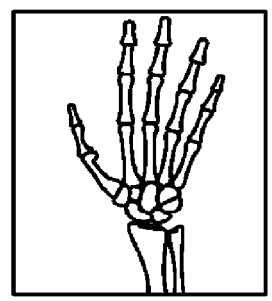
FIG.4C
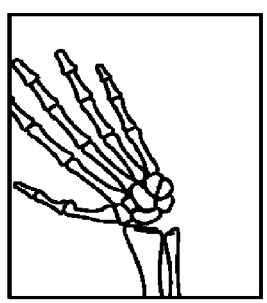 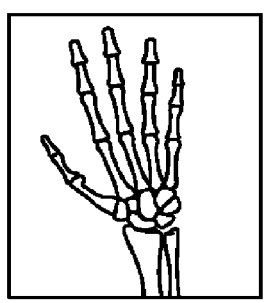 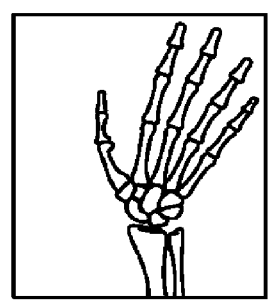

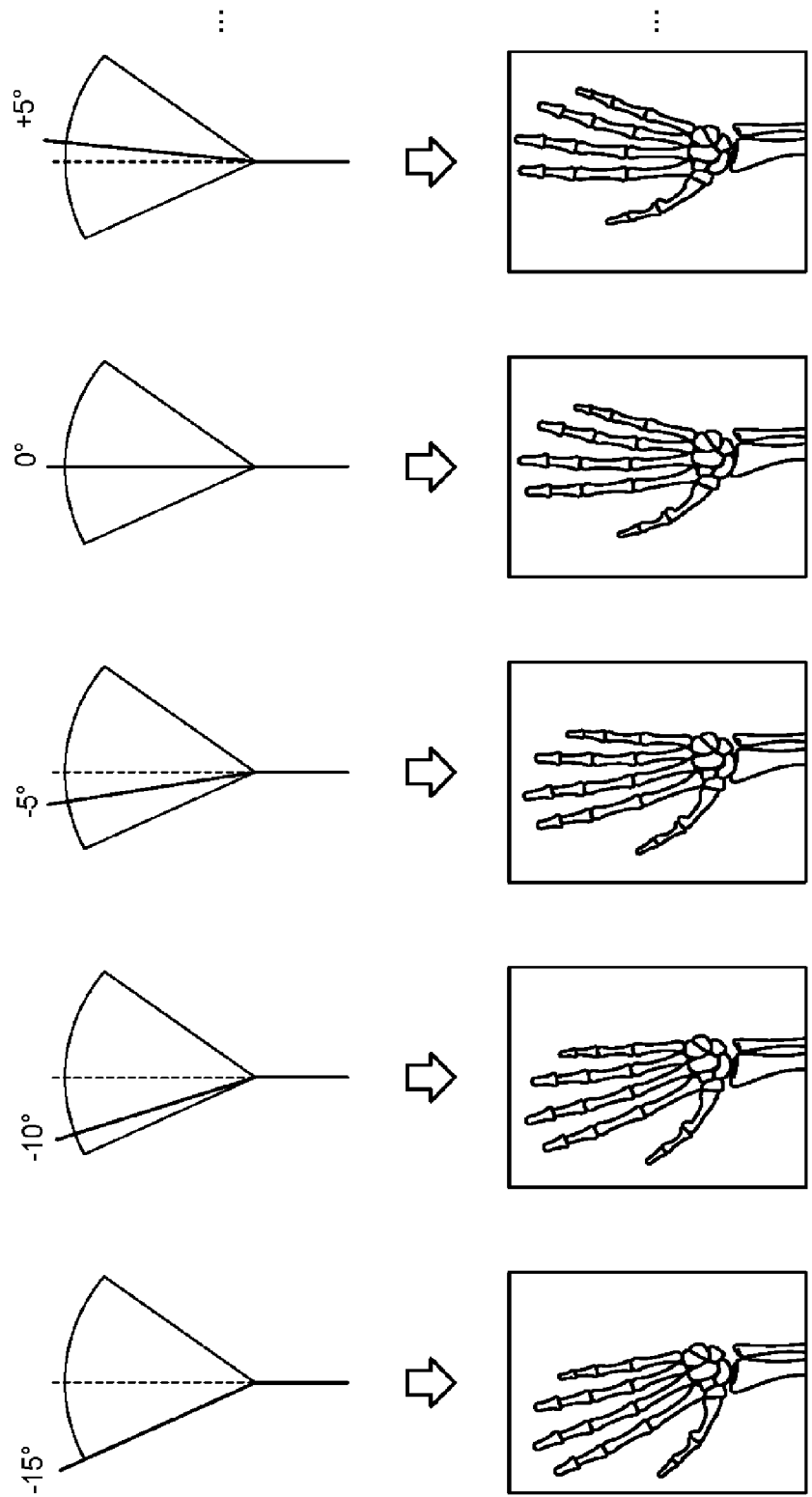

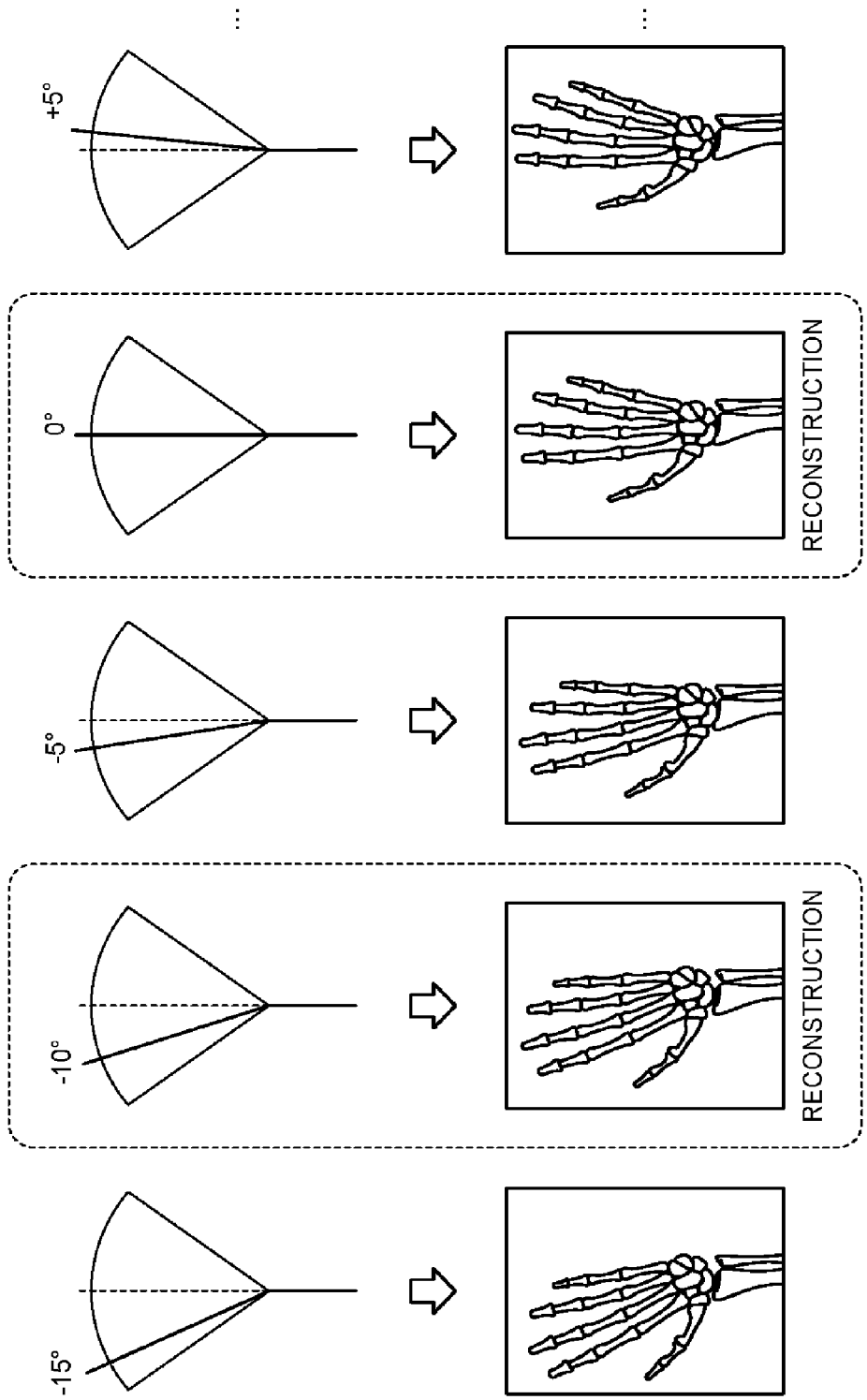

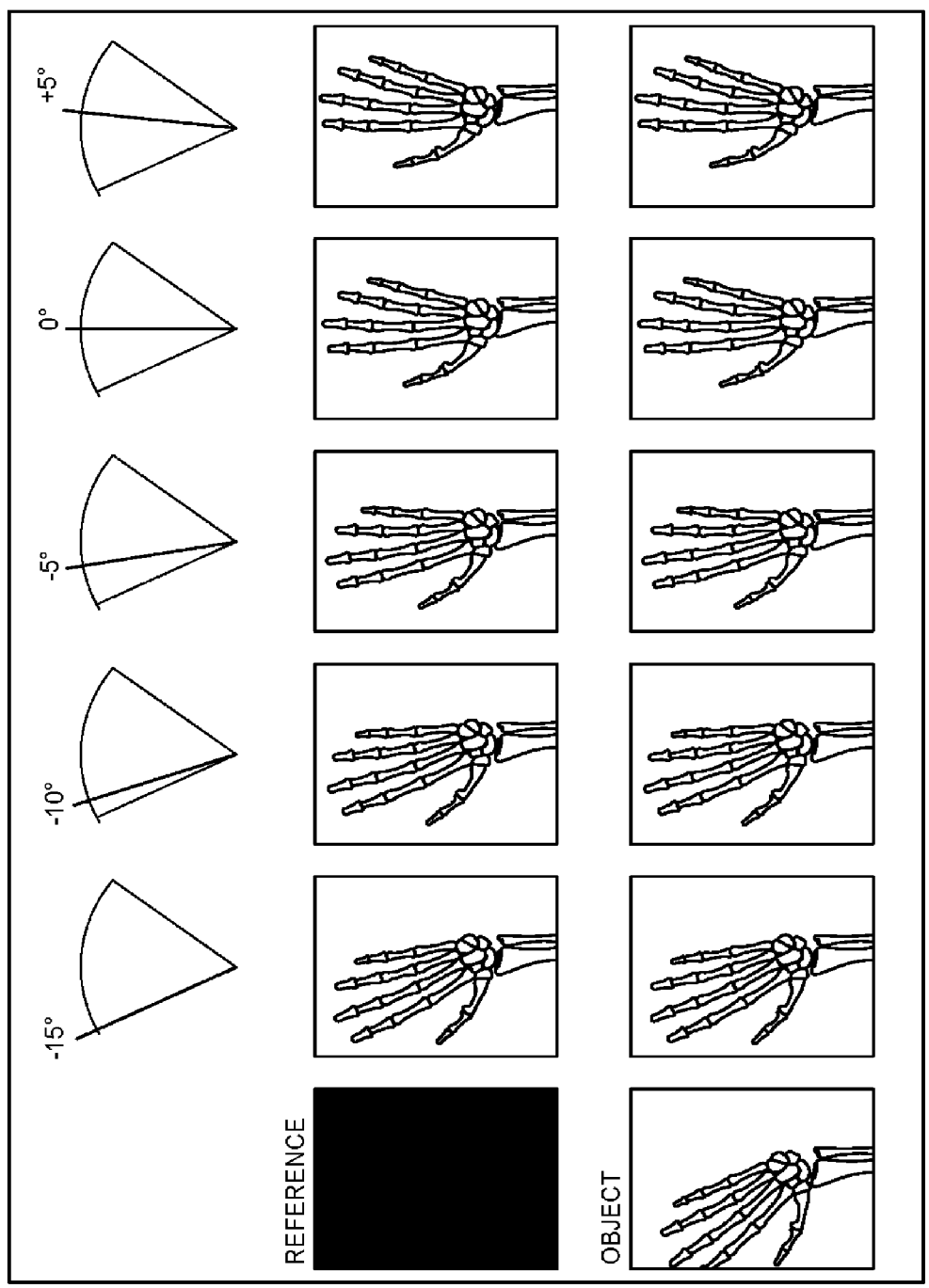

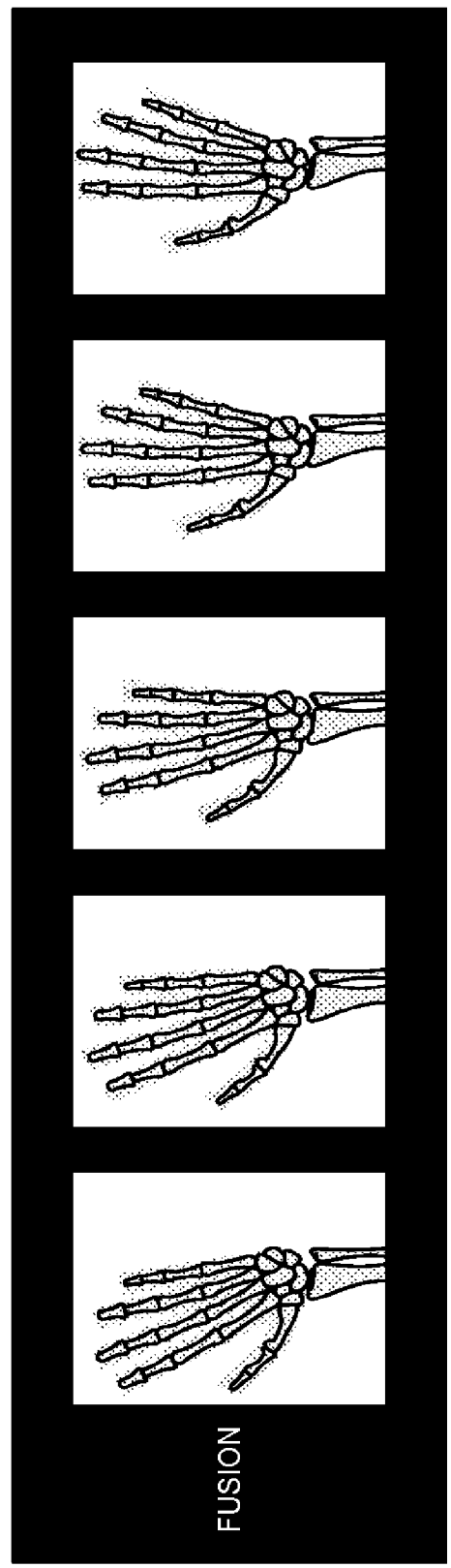

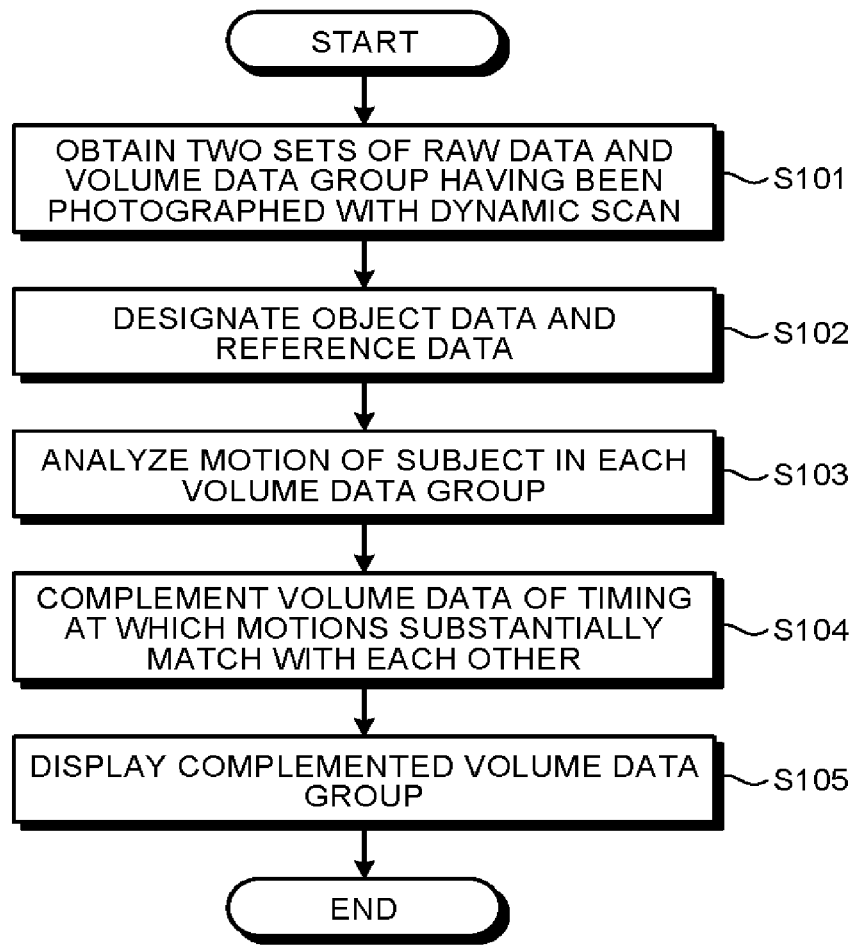

MEDICAL IMAGE PROCESSING APPARATUS AND METHOD FOR MEDICAL IMAGE PROCESSING

CROSS-REFERENCE TO RELATED APPLICATIONS

This application is based upon and claims the benefit of priority from Japanese Patent Application No. 2014-166686, filed on Aug. 19, 2014, the entire contents of all of which are incorporated herein by reference.

FIELD

Embodiments described herein relate generally to a medical image processing apparatus and a method for medical image processing.

BACKGROUND

An X-ray computed tomography (CT) apparatus creates an image of the inside of a subject by scanning the subject using X-rays and performing computer processing on collected data. An exemplary X-ray CT apparatus emits x-rays onto a subject from different directions and detects a signal of the X-rays having penetrated the subject with an X-ray detection element. The X-ray CT apparatus collects the detected signal, converts the analogue signal to a digital signal, performs preprocessing and others, and generates raw data. The X-ray CT apparatus performs reconstruction processing based on the raw data and generates an image.

Such a dynamic volume scan has been developed with an X-ray computed tomography (CT) apparatus that repeatedly rotates a rotary frame while having X-rays emitted for a certain time and photographs a plurality of three-dimensional volume data pieces at a certain frame rate (volume rate). This kind of scan allows steric observation and assessment on a serial change of a specific part.

BRIEF DESCRIPTION OF THE DRAWINGS

FIGS. 4A to 4C are drawings for describing an issue;

FIGS. 7A and 7B are drawings for describing processing performed by an image complementing unit according to the first embodiment;

FIGS. 8A to 8D are drawings for describing processing performed by an output control unit according to the first embodiment; and FIG. 9 is a flowchart for describing processing performed by the medical image processing apparatus according to the first embodiment.

DETAILED DESCRIPTION

A medical image processing apparatus according to an embodiment includes processing circuitry. The processing circuitry obtains a plurality of medical image groups in which respective motions of a part inside a subject have been photographed in time series and executes certain processing on the acquired medical image groups. The processing circuitry analyzes the motions in the respective medical image groups. The processing circuitry generates a medical image in which the motions in the respective medical image groups substantially match with each other based on the analyzed motions.

First Embodiment

Figure 1:
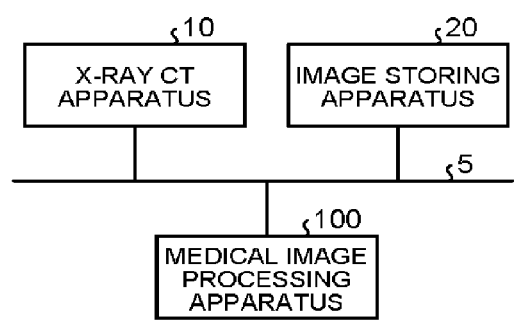
FIG. 1 is a drawing that illustrates an exemplary configuration of an image processing system according to a first embodiment.

FIG. 1 is a drawing that illustrates an exemplary configuration of an image processing system according to a first embodiment. As illustrated in FIG. 1, the image processing system according to the first embodiment includes an X-ray computed tomography (CT) apparatus 10, an image storing apparatus 20, and a medical image processing apparatus 100. The apparatuses illustrated in FIG. 1 are in a state of being directly or indirectly communicable with one another via, for example, an in-hospital local area network (LAN) 5 deployed in a hospital. If a picture archiving and communication system (PACS) is adopted for the image processing system, the apparatuses mutually transmit and receive medical image data and the like to and from one another in accordance with the digital imaging and communications in medicine (DICOM) standard.

FIG. 1 is only an example, and in addition to the apparatuses illustrated in FIG. 1, the image processing system may include another medical image diagnostic apparatus such as an X-ray diagnostic apparatus, an ultrasonic diagnostic apparatus, and a magnetic resonance imaging (MRI) apparatus.

The X-ray CT apparatus 10 has a rotary frame that is rotatable while supporting an X-ray tube emitting X-rays and an X-ray detector detecting the X-rays having penetrated a subject at respective positions facing each other. The X-ray CT apparatus 10 rotates the rotary frame while having the X-ray tube emit X-rays and collects data of the X-rays having undergone penetration, absorption, and attenuation. The X-ray CT apparatus 10 converts the collected data from analogue data to digital data (A/D conversion), performs correcting processing such as a logarithmic transformation, an offset correction, a sensitivity correction, a beam hardening correction, and a scatter correction, and generates raw data. The X-ray CT apparatus 10 reconstructs the generated raw data and generates three-dimensional volume data. Volume data is an example of medical image data.

The image storing apparatus 20 is a database that stores therein medical image data. Specifically, the image storing apparatus 20 stores volume data generated by the X-ray CT apparatus 10 in a memory unit in the image storing apparatus 20 and keeps the data. Volume data is stored in the image storing apparatus 20, for example, in a manner associated with additional information such as a patient ID, an examination ID, apparatus ID, and a series ID.

Examples of the medical image processing apparatus 100 include a workstation and a personal computer (PC) used by doctors and laboratory technicians working for the hospital for reviewing medical images. An operator of the medical image processing apparatus 100 performs a search using information such as a patient ID, an examination ID, apparatus ID, and a series ID and obtains necessary medical image data from the image storing apparatus 20 or the X-ray CT apparatus 10. In another case, the medical image processing apparatus 100 may directly receive medical image data from the X-ray CT apparatus 10. In addition to displaying medical image data for reference, the medical image processing apparatus 100 may perform various kinds of image processing on the medical image data.

Figure 2:
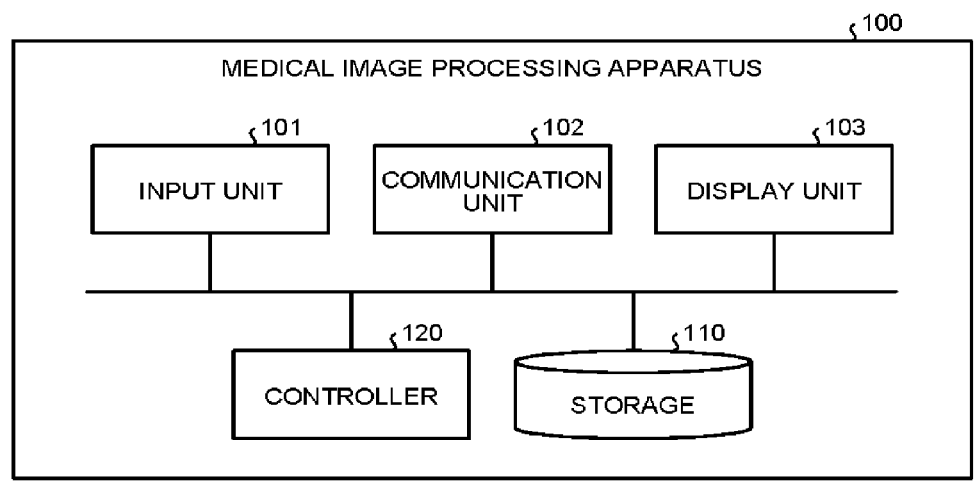
FIG. 2 is a drawing that illustrates an exemplary configuration of a medical image processing apparatus according to the first embodiment.

FIG. 2 is a drawing that illustrates an exemplary configuration of the medical image processing apparatus 100 according to the first embodiment. As FIG. 2 illustrates, the medical image processing apparatus 100 includes an input unit 101, a communication unit 102, a display unit 103, a memory unit 110, and a control unit 120. The input unit 101, the communication unit 102, the display unit 103, the memory unit 110, and the control unit 120 are connected with one another.

Examples of the input unit 101 include a mouse, a keyboard, and a truck ball, and the input unit 101 receives various kinds of operation input to the medical image processing apparatus 100 from the operator. Examples of the communication unit 102 include a network interface card (NIC), and the communication unit 102 communicates with other apparatuses. Examples of the display unit 103 include a monitor and a liquid crystal panel, and the display unit 103 displays various kinds of information.

Examples of the memory unit 110 include a hard disk and a semiconductor memory element, and the memory unit 110 stores therein various kinds of information. For example, the memory unit 110 stores therein various kinds of processing executed by the control unit 120.

Examples of the control unit 120 include an electronic circuit such as a central processing unit (CPU) and a micro processing unit (MPU) and an integrated circuit such as an application specific integrated circuit (ASIC) and a field programmable gate array (FPGA). The control unit 120 performs overall control on the medical image processing apparatus 100. The control unit 120 is an example of processing circuitry.

Figure 3:
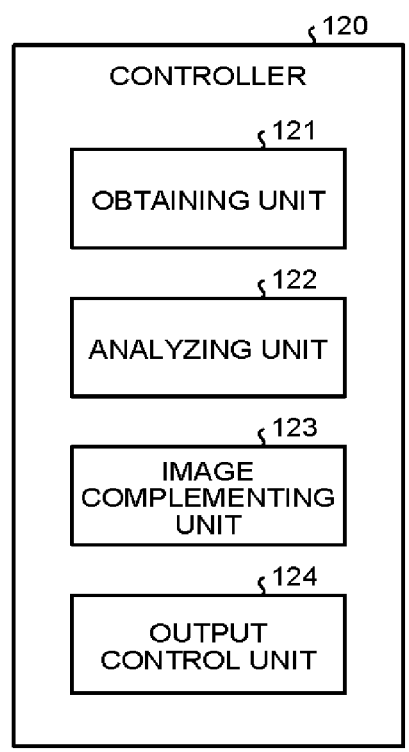
FIG. 3 is a functional block diagram for describing a function of a control unit according to the first embodiment.

FIG. 3 is a functional block diagram for describing a function of the control unit 120 according to the first embodiment. As FIG. 3 illustrates, the control unit 120 includes an obtaining unit 121, an analyzing unit 122, an image complementing unit 123, and an output control unit 124. The function of each unit included in the control unit 120 will be described later.

The X-ray CT apparatus 10 according to the first embodiment can perform a dynamic volume scan (hereinafter simply referred to as a "dynamic scan") that generates volume data at a certain frame rate by photographing a subject in time series. Specifically, the X-ray CT apparatus 10 performs a dynamic scan using an X-ray detector referred to as a multi-row detector having a plurality of X-ray detecting elements in the channel direction (the row direction) and in the slicing direction (the column direction). Use of the dynamic scan makes it possible to observe motions of a bone and a ligament during a joint movement. For example, by performing a dynamic scan on and around the right wrist of a patient (a subject) having injured a ligament of the right wrist, it is possible to observe the position and the direction of the carpal bones corresponding to the direction of the right hand and diagnose the condition of the ligament of the right wrist.

However, it may be difficult to observe volume data photographed in a dynamic scan in a manner of comparing with volume data photographed in another dynamic scan. For example, comparative observation between volume data photographed in a previous examination and volume data photographed in the current examination may be difficult because no volume data is shared between both volume data. Such no presence of volume data shared between both volume data is attributed to the fact that dynamic scan reconstructs volume data with some pieces of volume data removed.

Figure 4A:
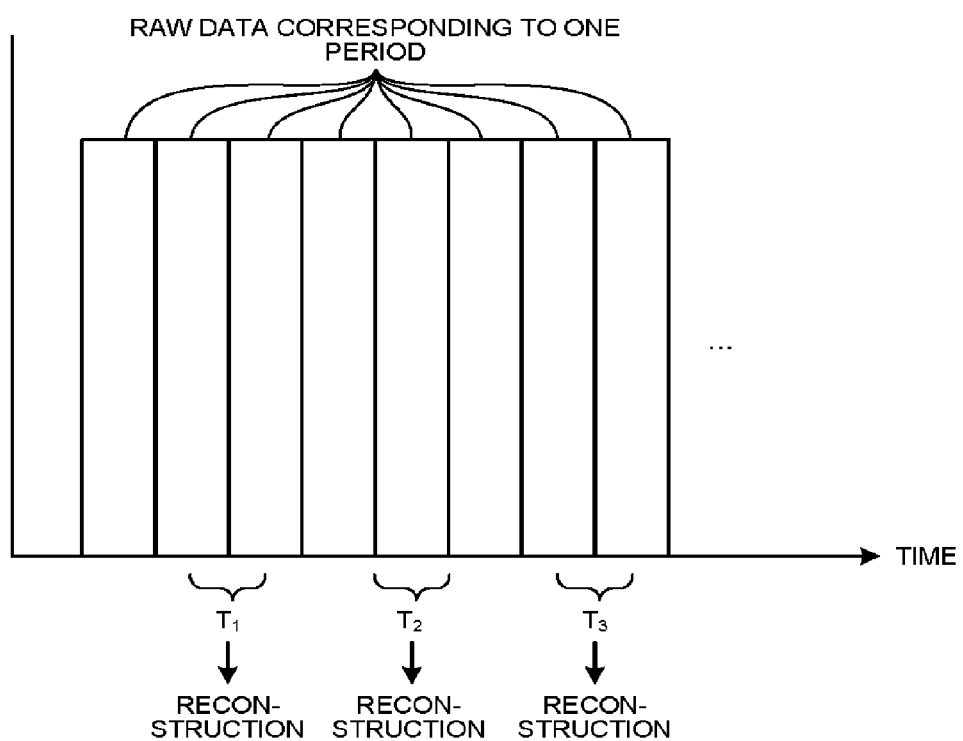

FIGS. 4A to 4C are drawings for describing an issue. FIG. 4A is a drawing for describing the relation between raw data and reconstruction in a dynamic scan, and the lateral direction represents the time course. FIGS. 4B and 4C are examples of volume rendering (VR) images in a series of volume data representing radial and ulnar flexion motions of a right hand photographed with a dynamic scan. Specifically, in each of FIGS. 4B and 4C, the VR images are aligned in time series from the left side of the drawing and depict a hand of a subject changing from the state of inclining toward the thumb side (radial flexion) to the state of inclining toward the little-finger side (ulnar flexion). FIG. 4B is an example of VR images photographed in a previous examination (dynamic scan) whereas FIG. 4C is an example of VR images photographed in the current examination.

As FIG. 4A illustrates, for example, the X-ray CT apparatus 10 repeatedly rotates the rotary frame while having X-rays emitted onto a subject moving a joint and sequentially generates raw data corresponding to one period of the rotary frame. The X-ray CT apparatus 10 performs reconstruction using the generated raw data. In this process, the X-ray CT apparatus 10 performs no reconstruction on a part of the raw data and reconstructs data at a certain interval so as to control the increase in the amount of data and the load of processing. In the example illustrated in FIG. 4A, the X-ray CT apparatus 10 reconstructs raw data corresponding to each of periods $T_1$, $T_2$, and $T_3$ and generates a volume data group including a plurality of volume data pieces representing a sequential motion of the joint (see FIGS. 4B and 4C).

In this manner, respective volume data groups relating to a previous examination and the current examination are generated as illustrated in FIGS. 4B and 4C. Both generated volume data groups are merely data reconstructed at a certain interval (a volume rate or a frame rate), and timings to start the motions, ranges of the motions, velocities of the motions, and the like do not necessarily match between both groups. For this reason, when a previous VR image and a current VR image are aligned, it is not necessarily the case that the directions of the right hand in the respective VR images match with each other. Thus, when a doctor needs to compare the position and the direction of each carpal bone of the right hand radially flexed in a certain direction, volume data with the right hand radially flexed in the direction does not necessarily exist in each of the previous examination and the current examination. Comparative observations therefore may be difficult.

As a solution to the above-described problem, the volume rate may be increased by complementing between volumes. However, simply increasing the volume rate in a time unit (for example, increasing the rate from 30 fps to 60 fps) does not necessarily match the directions of the right hand between the previous examination and the current examination. Simply increasing the volume rate is thus not a fundamental solution.

The medical image processing apparatus 100 according to the embodiment therefore has the following functions so as to facilitate comparative observation between three-dimensional medical image data having been photographed in time series.

In the first embodiment, an exemplary case is described where radial and ulnar flexion motions of the right hand of a subject are photographed with a dynamic scan in each of a previous examination and the current examination and images photographed in both examinations are compared.

The embodiment is, however, not limited thereto. Examples of a motion of a subject are not limited to radial and ulnar flexion motions but may include other joint motions such as palmar and dorsal flexion motions of a hand, inward and outward bending motions of a foot, flexion and extension motions of a knee. Furthermore, images used for comparative observation are not limited to images of a single subject. Images of two different subjects such as a patient and a healthy subject may be compared. The number of images to be compared is not limited to two, and more than two images may be compared.

The obtaining unit 121 obtains at least two volume data groups that each includes a plurality of volume data pieces in which a motion of a subject has been photographed in time series. The obtaining unit 121 further obtains data before reconstruction corresponding to each of at least two volume data groups. Volume data is an example of a three-dimensional medical image data. A processing circuit including the obtaining unit 121 obtains a plurality of three-dimensional medical image groups in which respective motions of a part inside a subject have been photographed in time series and performs specific processing on the obtained three-dimensional medical image groups.

For example, an operator operates the input unit 101 and designates two pieces of examination data to be compared with each other. Specifically, the operator designates a patient ID of a subject and an examination ID of the current examination as object data (data for diagnosis) and designates an examination ID of a previous examination of the subject as reference data (data for reference). In this case, the obtaining unit 121 obtains a set consisting of a volume data group having been photographed in the current examination and raw data corresponding to the volume data group from the image storing apparatus 20 using the designated patient ID and the examination ID of the current examination. The obtaining unit 121 further obtains another set consisting of a volume data group having been photographed in the previous examination and raw data corresponding to the volume data group from the image storing apparatus 20 using the designated patient ID and the examination ID of the previous examination. Sets each consisting of a volume data group photographed with a dynamic scan in an examination conducted in the hospital and raw data corresponding to the volume data group are stored in the image storing apparatus 20.

The above-described processing performed by the obtaining unit 121 is only an example. For example, the obtaining unit 121 may obtain examination data to be compared not only from the image storing apparatus 20 but also from the X-ray CT apparatus 10. For example, if examination data to be compared is recorded in a digital versatile disc (DVD), the obtaining unit 121 may read out the examination data recorded in the DVD and obtain the data.

The analyzing unit 122 analyzes motions of a subject in at least two obtained three-dimensional medical image data groups. For example, the analyzing unit 122 analyzes the ranges of the motions of the subject and the velocities of the motions in respective volume data groups of a previous examination and the current examination.

Figure 5:
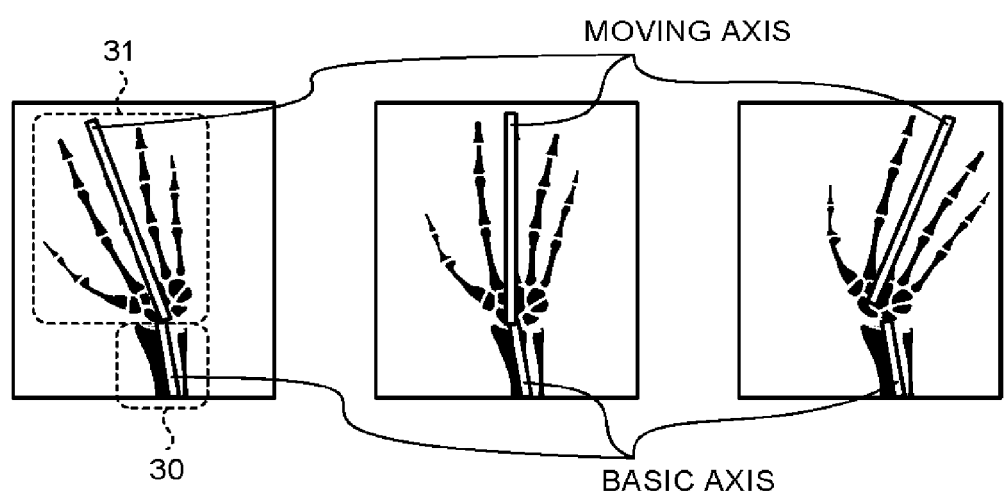
FIG. 5 is a drawing for describing processing performed by an analyzing unit according to the first embodiment.
Figure 6A:
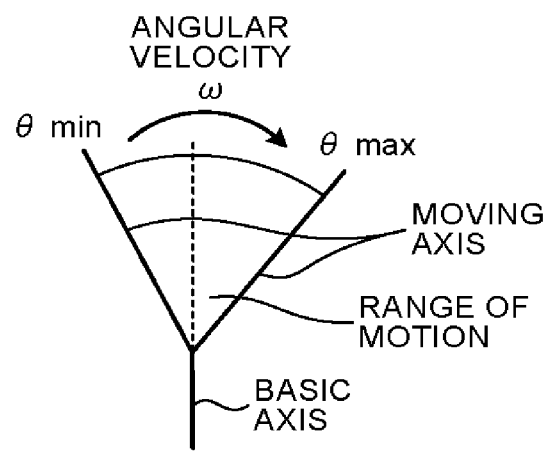
FIGS. 6A and 6B are drawings for describing processing performed by the analyzing unit according to the first embodiment.
Figure 6B:
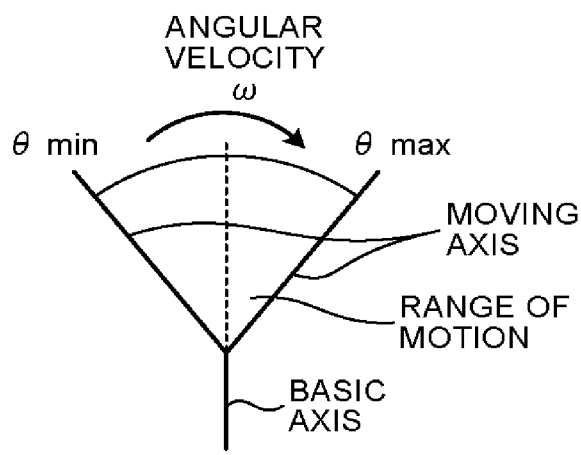

FIGS. 5, 6A, and 6B are drawings for describing processing performed by the analyzing unit 122 according to the first embodiment. FIG. 5 illustrates a binary image of volume data photographed in the previous examination. FIG. 6A is a schematic view of a joint movable range (the range in which the moving axis moves) of radial and ulnar flexion motions of a subject in the previous examination. FIG. 6B is a schematic view of a joint movable range of radial and ulnar flexion motions of the subject in the current examination.

The analyzing unit 122 detects a basic axis, which is an axis (a bone) the position of which is kept unchanged in the joint movement. For example, as FIG. 5 illustrates, the analyzing unit 122 binarizes a VR image of each volume data having been photographed in the previous examination. The analyzing unit 122 averages the binarized binary images, extracts a group of pixels existing in all the binary images, and extracts a forearm bone from each binary image (see a region 30 in FIG. 5). The analyzing unit 122 thereafter thins the extracted forearm bone and detects the basic axis. A bone locking processing technique may be adopted prior to detection of the basic axis. For example, the analyzing unit 122 may extract bones in a region to be observed with segmentation, lock a bone serving as a standard from among the extracted bones, and obtain motions of other bones.

The analyzing unit 122 detects a moving axis, which is an axis (a bone) the position of which is changed in the joint movement. For example, the analyzing unit 122 masks the extracted forearm bone in a binary image of a specific time and extracts the right hand bones (see a region 31 in FIG. 5). The analyzing unit 122 thereafter detects a line segment connecting two points located farthest from each other in the region of the extracted right hand bones as a moving axis. The analyzing unit 122 performs the same processing on each of other binary images and extracts moving axes from all the binary images.

The analyzing unit 122 calculates the range of the motion and the velocity of the motion. For example, as FIG. 6A illustrates, the analyzing unit 122 overlaps (summates) all the detected moving axes and specifies a range in which all the moving axes exist as a motion range. The analyzing unit 122 calculates the motion velocity based on the time at which the image having a minimum value ($\theta$min) of a motion angle has been photographed and the time at which the image having a maximum value ($\theta$max) of the motion angle has been photographed. The motion angle is an angle made by the basic axis and the moving axis. For example, the angle made in radial flexion is represented as a minus angle whereas the angle made in ulnar flexion is represented as a plus angle. In other words, the analyzing unit 122 calculates an angular velocity $\omega$ as a motion velocity by subtracting $\theta$min from $\theta$max and dividing the value after subtraction by a time spent from $\theta$min to $\theta$max.

In this manner, the analyzing unit 122 analyzes the motion range and the motion velocity of the previous examination in the volume data group having been photographed in the previous examination. The analyzing unit 122 performs the same processing as the processing performed on the volume data group having been photographed in the previous examination, and, as FIG. 6B illustrates, analyzes the motion range and the motion velocity of the current examination. The processing is the same as that described with reference to FIGS. 5 and 6A, and description is thus omitted. Consequently, the processing circuit including the analyzing unit 122 analyzes motions in a plurality of three-dimensional medical image groups.

The image complementing unit 123 complements, based on the analyzed motions of a subject, three-dimensional medical image data of a timing at which the motions of the subject in respective at least two three-dimensional medical image data groups substantially match with each other. For example, the image complementing unit 123 generates three-dimensional medical image data of a timing at which a part involved in the motions moves to a certain angle based on the motion ranges and the motion velocities. In other words, the processing circuit including the image complementing unit 123 generates three-dimensional medical image data of a timing at which a joint of a subject involved in the motions moves to a certain angle.

FIGS. 7A and 7B are drawings for describing processing performed by the image complementing unit 123 according to the first embodiment. FIG. 7A illustrates an example of processing performed on a volume data group having been photographed in the previous examination. FIG. 7B illustrates an example of processing performed on a volume data group having been photographed in the current examination.

In the examples illustrated in FIGS. 7A and 7B, such a case is described where the image complementing unit 123 complements volume data of the current examination according to the direction of the right hand in volume data having been reconstructed in the previous examination.

The image complementing unit 123 specifies a direction of the right hand to be complemented. Such cases are now described where the directions (the angles made by the basic axis and the moving axis) of the right hand in volume data having been reconstructed in the previous examination are −15 degrees, −10 degrees, −5 degrees, 0 degrees, and +5 degrees (FIG. 7A). Furthermore, such cases are described where the directions of the right hand in volume data having been reconstructed in the current examination are −15 degrees, −5 degrees, and +5 degrees (FIG. 7B). From among the directions of the right hand having been reconstructed in the previous examination, directions of −10 degrees and 0 degrees are not reconstructed in the current examination (the areas indicated with the dashed lines in FIG. 7B). The image complementing unit 123 specifies these directions as directions of the right hand to be complemented. In other words, the processing circuit including the image complementing unit 123 calculates, based on the motion ranges and the motion velocities, that a joint involved in the motions is at a certain angle.

The image complementing unit 123 calculates the time of photographing corresponding to the specified direction of the right hand. For example, the image complementing unit 123 calculates the time of photographing corresponding to the specified direction of the right hand using the following Formula 1.

$$t[\sec] = \frac{\theta[\text{rad}]}{\omega[\text{rad/sec}]} \quad (1)$$

In Formula 1, t [sec] represents an elapsed time after starting photographing. θ [rad] represents the amount of displacement in the direction (the angle made by the basic axis and the moving axis) of the right hand after starting photographing. ω [rad/sec] represents the angular velocity, which corresponds to the motion velocity calculated by the analyzing unit 122. For example, if the direction of the right hand after starting photographing is −25 degrees, the image complementing unit 123 calculates the amount of displacement until the direction reaches −10 degrees to be +15 degrees (π/12 [rad]). If the angular velocity in the current examination calculated by the analyzing unit 122 is π/18 [rad/sec], the image complementing unit 123 calculates the elapsed time after starting photographing to be 1.5 [sec]. The image complementing unit 123 calculates the time of photographing corresponding to the specified direction of the right hand by adding the elapsed time to the time of starting photographing. Likewise, the image complementing unit 123 calculates the time of photographing at which the direction of the right hand is 0 degrees.

The image complementing unit 123 reconstructs volume data corresponding to the calculated time of photographing from raw data collected in the current examination. As FIG. 4A illustrates, the raw data includes projection data collected from the start to the end of photographing, and it is thus possible to reconstruct volume data corresponding to any time of photographing. In this manner, the image complementing unit 123 complements volume data pieces corresponding to respective directions of −10 degrees and 0 degrees of the right hand (the areas indicated with the dashed lines in FIG. 7B). Raw data is an example of data before reconstruction.

From data pieces before reconstruction corresponding to respective two three-dimensional medical image data groups, the image complementing unit 123 reconstructs three-dimensional medical image data of a timing at which motions of a subject substantially match with each other. FIGS. 7A and 7B are only examples. Although such a case has been described where the image complementing unit 123 complements volume data in the current examination according to the direction of the right hand in the previous examination, the embodiment is not limited thereto. Conversely, for example, the image complementing unit 123 may complement volume data in the previous examination according to the direction of the right hand in the current examination. In another case, for example, the image complementing unit 123 may generate volume data in the previous and the current examinations according to any direction designated by the operator even if reconstruction has been performed in neither the previous examination nor the current examination. Consequently, based on the analyzed motions, the processing circuit including the image complementing unit 123 generates a three-dimensional medical image in which the motions in respective three-dimensional medical image groups substantially match with each other.

The output control unit 124 outputs two three-dimensional medical image data groups complemented by the image complementing unit 123 in such a manner that motions of a subject substantially match with each other.

For example, the output control unit 124 displays, in time series or in a replay mode, a plurality of output image data pieces made from each of the complemented two volume data groups. In another case, the output control unit 124 displays, in time series or in a replay mode, a plurality of superimposed image data pieces in which a plurality of output image data pieces made from each of two volume data groups are superimposed on each other based on a timing at which motions of a subject substantially match. In another case, the output control unit 124 further displays at least one of a motion range, a motion velocity, and a direction of a specific part involved in the motions.

Figure 8B:
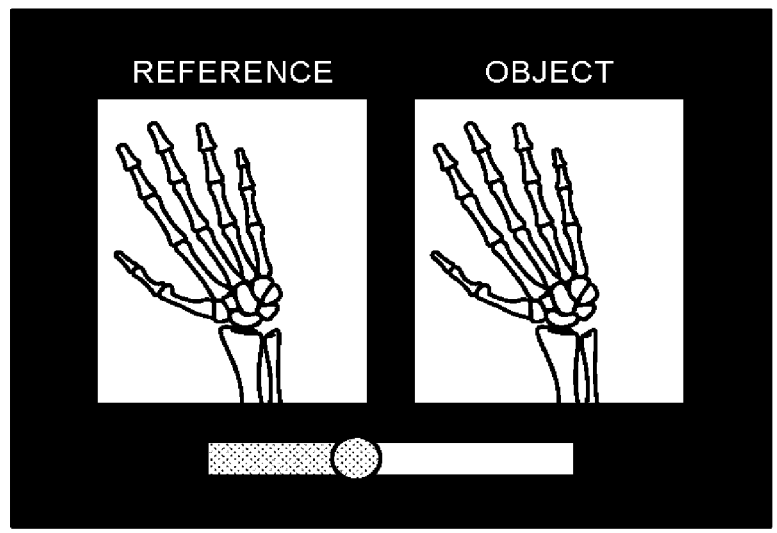
Figure 8D:
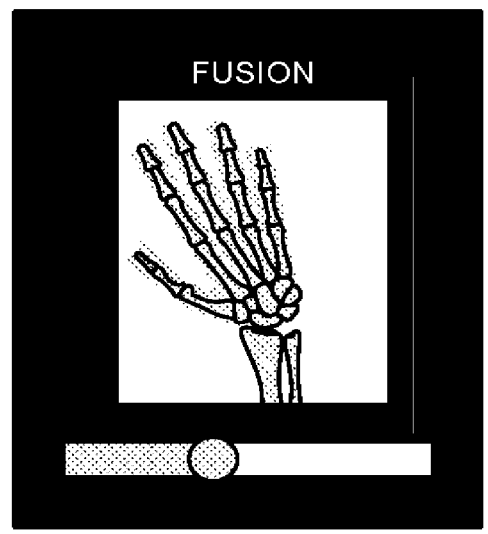

FIGS. 8A to 8D are drawings for describing processing performed by the output control unit 124 according to the first embodiment. FIG. 8A illustrates an exemplary case where images in each of the volume data groups are displayed in parallel. FIG. 8B illustrates an exemplary case where images in each of the volume data groups are replayed in the cine play mode. FIG. 8C illustrates an exemplary case where superimposed images made from the volume data groups are displayed in parallel. FIG. 8D illustrates an exemplary case where superimposed images made from the volume data groups are replayed in the cine play mode. A plurality of display modes displayed by the output control unit 124 are described with reference to FIGS. 8A to 8D; however, any one of the display modes may be used for actual display.

As FIG. 8A illustrates, the output control unit 124 displays, as references, VR images generated from the volume data group in the previous examination in a manner of aligning the images in time series and further displays, as objects, VR images generated from the volume data group in the current examination in a manner of aligning the images in time series. In this process, the output control unit 124 displays VR images in such a manner that the position of the basic axis of a VR image in the previous examination matches the position of the basic axis of a VR image in the current examination. The output control unit 124 further displays an image indicating the motion range of the right hand, an image indicating the moving axis of the right hand, and a value indicating the angle of the right hand in order to accurately depict the direction of the right hand in each of the VR images. The area painted in black positioned at the bottom left of FIG. 8A indicates that there is no corresponding VR image in the reference because the object covers a larger motion range.

As FIG. 8B illustrates, the output control unit 124 displays, as a reference, each VR image generated from the volume data group in the previous examination in a replay mode using the cine play and displays, as an object, each VR image generated from the volume data group in the current examination in a replay mode.

As FIG. 8C illustrates, the output control unit 124 generates superimposed image data in which a VR image serving as a reference and generated from the volume data group in the previous examination and another VR image generated from the volume data group in the current examination are superimposed on each other. The output control unit 124 thereafter displays the generated superimposed image data in a manner aligned in time series (Fusion).

As FIG. 8D illustrates, the output control unit 124 displays superimposed image data generated in a similar manner with FIG. 8C in a replay mode using the cine play.

In this manner, in various kinds of display modes, the output control unit 124 displays image data pieces made from respective volume data groups based on a timing at which motions in the respective volume data groups substantially match with each other.

FIG. 8A is only an example. In FIGS. 8A to 8D, such a case has been described where a VR image based on volume data is displayed for example; however, the embodiment is not limited thereto. For example, the output control unit 124 may generate a multi planar reconstructions (MPR) image based on volume data and display the generated MPR image in the display modes of FIGS. 8A to 8D.

In FIG. 8A, such a case has been described where the output control unit 124 displays an image indicating the motion range of a right hand, an image indicating the moving axis of the right hand, and a value indicating the angle of the right hand; however, the embodiment is not limited thereto. For example, the output control unit 124 does not display one or all of the images and the value. Alternatively, the output control unit 124 may further display a value indicating the motion velocity. The output control unit 124 may display the motion range, the motion velocity, the direction of a specific part involved in the motions, and the like not only in the case of FIG. 8A but also in the cases of FIGS. 8B to 8D.

FIG. 9 is a flowchart for describing processing performed by a medical image processing apparatus according to the first embodiment. As FIG. 9 illustrates, the medical image processing apparatus 100 obtains two sets of raw data and a volume data group having been photographed with a dynamic scan (Step S101). The medical image processing apparatus 100 designates object data and reference data (Step S102).

The medical image processing apparatus 100 thereafter analyzes the motion of a subject in each of the volume data groups (step S103). For example, the medical image processing apparatus 100 analyzes the motion range and the motion velocity of the subject in the volume data group in each of the previous examination and the current examination.

The medical image processing apparatus 100 complements volume data of a timing at which motions substantially match with each other (Step S104). For example, based on the motion ranges and the motion velocities, the medical image processing apparatus 100 generates three-dimensional medical image data corresponding to a time of photographing at which a part involved in the motions moves to a certain angle.

The medical image processing apparatus 100 thereafter displays each of the complemented volume data groups (Step S105). For example, the medical image processing apparatus 100 displays, in various kinds of display modes, image data (such as a VR image) made from each of the volume data groups based on a timing at which motions in the respective volume data groups substantially match with each other.

FIG. 9 is only an example. For example, the processing at Step S105 for displaying complemented volume data groups is not necessarily performed. In other words, the medical image processing apparatus 100 may store the volume data groups having been complemented in the processing at Step S104 in any memory device. With this process, the doctor can review images in which motions of a subject substantially match with each other when the doctor desires.

As described above, the medical image processing apparatus 100 according to the first embodiment obtains at least two three-dimensional medical image data groups each including a plurality of three-dimensional medical image data pieces in which a motion of a subject has been photographed in time series. The medical image processing apparatus 100 analyzes the motion of the subject in each of the obtained at least two three-dimensional medical image data groups. Based on the analyzed motion of the subject, the medical image processing apparatus 100 thereafter complements three-dimensional medical image data of a timing at which the motions of the subject in the respective at least two three-dimensional medical image data groups substantially match with each other. In this manner, the medical image processing apparatus 100 facilitates comparative observation between three-dimensional medical image data having been photographed in time series.

For example, with the medical image processing apparatus 100 according to the first embodiment, such images can be reviewed in which motions of a subject substantially match with each other between volume data groups having been photographed in two or more different examinations. This configuration enables a doctor, for example, to compare the positions and directions of a carpal bone in different examinations with the right hand radially flexed in a certain direction, which may achieve more efficient and accurate observation.

Second Embodiment

In the first embodiment as described above, the medical image processing apparatus 100 reconstructs volume data of a timing at which motions substantially match with each other from raw data, which is data before reconstruction; however, the embodiment is not limited thereto. For example, the medical image processing apparatus 100 may generate volume data of a timing at which motions substantially match with each other from reconstructed volume data.

For example, raw data covering the whole period in which a subject is making a motion is not always available. With a dynamic scan, for example, X-rays may be emitted exclusively in periods (for example, periods $T_1$, $T_2$, and $T_3$ in FIG. 4A) in which image reconstruction is planned in order to suppress the amount of exposure of a subject to X-rays. In this case, raw data of a timing at which motions of the subject substantially match with each other is not necessarily included in raw data stored in the image storing apparatus 20. Reconstruction cannot be performed without raw data, and it may be therefore useful, as described in the following description, to generate volume data of a timing at which motions substantially match with each other from reconstructed volume data.

The medical image processing apparatus 100 according to a second embodiment has the same configuration (FIG. 2) and the same function (FIG. 3) as those of the medical image processing apparatus 100 described in the first embodiment; however, the processing performed by the image complementing unit 123 is partly different. Points shared with the first embodiment will be thus omitted from description in the second embodiment, and different points will be particularly described.

As described in the first embodiment, the image complementing unit 123 according to the second embodiment specifies the direction of a part (such as a right hand) to be complemented and calculates the time of photographing corresponding to the specified direction of the part. The image complementing unit 123 according to the second embodiment thereafter generates three-dimensional medical image data of a timing at which motions of the subject substantially match with each other from three-dimensional medical image data pieces included in respective two (or more) three-dimensional medical image data groups to be compared.

For example, the image complementing unit 123 generates, from existing volume data, volume data of a timing at which motions of a subject substantially match with each other using an affine transformation.

Such a case is now described that generates, with an affine transformation, volume data of a timing at which the direction of a right hand is −10 degrees in the current examination. In this case, the image complementing unit 123 selects volume data of a timing at which the direction of the right hand is closest to −10 degrees from the volume data group in the current examination. For example, the image complementing unit 123 selects volume data of a timing at which the direction of the right hand is −15 degrees from the volume data group in the current examination. The image complementing unit 123 thereafter rotates and moves pixels composing bones of the right hand in the volume data of a timing at which the direction of the right hand is −15 degrees until the direction of the right hand becomes −10 degrees. In this process, the image complementing unit 123 does not move pixels corresponding to the forearm bone serving as a basic axis. In this manner, the image complementing unit 123 generates volume data of a timing at which the direction of the right hand is −10 degrees.

In this manner, the medical image processing apparatus 100 according to the second embodiment generates volume data of a timing at which motions substantially match with each other from reconstructed volume data. Consequently, the medical image processing apparatus 100 can generate volume data of a timing at which motions substantially match with each other without raw data of a timing at which motions of a subject substantially match with each other.

In the second embodiment, the medical image processing apparatus 100 generates volume data of a timing at which motions substantially match with each other without using raw data. The obtaining unit 121 of the medical image processing apparatus 100 therefore has no necessity to obtain raw data corresponding to a volume data group.

Other Embodiments

The first and the second embodiments have been described as above; however, embodiments may be implemented in various different modes other than the first and the second embodiments.

For example, in the first and the second embodiments, the medical image processing apparatus 100 has functions to facilitate comparative observations between three-dimensional medical image data each having been photographed in time series. The embodiments are not limited thereto. For example, by applying similar functions to the X-ray CT apparatus 10, the X-ray CT apparatus 10 may have above-described functions and execute processing to facilitate comparative observations between three-dimensional medical image data each having been photographed in time series.

Furthermore, in the first and the second embodiments, such a case has been described where the medical image processing apparatus 100 executes a process using three-dimensional medical image data group. However, the embodiments are not limited thereto. For example, the medical image processing apparatus 100 may execute a process using two-dimensional medical image data group including a plurality of two-dimensional medical image data pieces. For example, a medical image processing apparatus 100 according to an embodiment includes processing circuitry. The processing circuitry obtains a plurality of two-dimensional medical image groups in which respective motions of a part inside a subject have been photographed in time series and executes certain processing on the acquired two-dimensional medical image groups. The processing circuitry analyzes the motions in the respective two-dimensional medical image groups. The processing circuitry generates a two-dimensional medical image in which the motions in the respective two-dimensional medical image groups substantially match with each other based on the analyzed motions.

Furthermore, functions of the obtaining unit 121, the analyzing unit 122, and the image complementing unit 123 described in the first and the second embodiments may be implemented with software. For example, functions of the obtaining unit 121, the analyzing unit 122, and the image complementing unit 123 may be implemented by causing a computer to execute a medical information processing program including prescribed procedures of processing, which has been described as processing performed by the obtaining unit 121, the analyzing unit 122, and the image complementing unit 123. The medical information processing program is executed in a manner stored in a hard disk, a semiconductor memory element, and the like, and read out by a processor such as a central processing unit (CPU) and a micro processing unit (MPU). Furthermore, the medical information processing program can be stored and provided in a computer-readable memory medium such as a compact disc-read only memory (CD-ROM), a magnetic optical disk (MO), and a digital versatile disc (DVD).

In the above embodiments, a motion of a joint is analyzed as a motion of a subject; however, the embodiments are not limited thereto. For example, the embodiments are applicable to a case of analyzing a motion of a diaphragm as a motion of a subject. An analysis of a motion of a diaphragm is used in observing a motion of breathing.

For example, the analyzing unit 122 calculates motion ranges and motion velocities in a plurality of three-dimensional medical image groups (of the previous examination and the current examination, for example). Specifically, the analyzing unit 122 specifies the range between the maximum position (height) of the thorax (for example, the breastbone) of a subject and the minimum position thereof as the motion range. The analyzing unit 122 thereafter calculates the motion velocity based on the time of photographing an image of a timing at which the thorax is in the minimum position and the time of photographing an image of a timing at which the thorax is in the maximum position. In this manner, the analyzing unit 122 calculates the motion ranges and the motion velocities in the respective three-dimensional medical image groups (of the previous examination and the current examination, for example).

Based on the motion ranges and the motion velocities, the image complementing unit 123 generates three-dimensional medical image data of a timing at which the thorax moves to a certain position. For example, based on the motion ranges and the motion velocities, the image complementing unit 123 calculates the time of photographing when the position of the thorax in the current examination moves to a position substantially matching the position of the thorax in the previous examination. The image complementing unit 123 reconstructs three-dimensional medical image data corresponding to the calculated time of photographing from data before reconstruction. In this manner, the image complementing unit 123 reconstructs three-dimensional medical image data in which positions of a thorax substantially match with each other in the previous examination and the current examination.

In this manner, the medical image processing apparatus 100 is applicable in analyzing a motion of a diaphragm. The medical image processing apparatus 100 may analyze a motion of a diaphragm by observing, for example, an interval between rib bones instead of observing an up-and-down motion of the thorax of a subject.

At least one of the embodiments described above exerts effects of facilitating a comparative observation between three-dimensional medical image data having been photographed in time series.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising: processing circuitry configured to
    obtain a plurality of medical image groups in which respective motions of a part inside a subject have been photographed in time series, and execute certain processing on the obtained medical image groups;
    analyze changes in an angle of the part involved in the motions in the respective medical image groups; and
    specify, based on the analyzed changes in the angle, a time at which the angle of the part is set to an angle that is substantially identical among the medical image groups; and
    generate a medical image corresponding to the specified time.

2. The medical image processing apparatus according to claim 1, wherein the processing circuitry is further configured to generate a medical image in which a joint of the subject involved in the motions is tilted to a certain angle.

3. The medical image processing apparatus according to claim 2, wherein the processing circuitry is further configured to
    analyze respective ranges of the motions and respective velocities of the motions, and
    calculate, based on the analyzed ranges of the motions and velocities of the motions, an elapsed time from a start time of imaging until the joint involved in the motions is tilted to a certain angle.

4. The medical image processing apparatus according to claim 1, wherein the processing circuitry is further configured to reconstruct, from pre-reconstruction data corresponding to each of the medical image groups, a medical image showing the part of the subject involved in the motions that is moved to the angle substantially identical among the medical image groups.

5. The medical image processing apparatus according to claim 1, wherein the processing circuitry is further configured to generate, from medical images included in the respective medical image groups, a medical image showing the part of the subject involved in the motions titled to the angle substantially identical among the medical image groups.

6. The medical image processing apparatus according to claim 1, wherein the processing circuitry is further configured to output each of the medical image groups in which the part of the subject involved in the motions is moved to the angle substantially identical among the medical image groups.

7. The medical image processing apparatus according to claim 6, wherein the processing circuitry is further configured to display each of the medical image groups generated in a manner aligned in time series or in a moving picture mode.

8. The medical image processing apparatus according to claim 6, wherein the processing circuitry is further configured to display in time series or in a moving picture mode, a plurality of superimposed images made by superimposing the medical images showing the part of the subject involved in the motions tilted to the angle substantially identical among the medical image groups.

9. The medical image processing apparatus according to claim 6, wherein the processing circuitry is further configured to display at least one of a range of the motions, a velocity of the motions, and a direction of a specific part involved in the motions.

10. A medical image processing method, comprising:
    obtaining a plurality of medical image groups in which respective motions of a part inside a subject have been photographed in time series, and executing certain processing on the obtained medical image groups;

analyzing changes in an angle of the part involved in the motions in the respective medical image groups;

specifying, based on the analyzed changes in the angle, a time at which the angle of the part is set to an angle that is substantially identical among the medical image groups; and generating a medical image corresponding to the specified time.

11. The medical image processing apparatus according to claim 1, wherein the respective medical image groups include a plurality of medical images that are reconstructed over time at a certain interval from raw data photographed in a dynamic scan using an X-ray computed tomography (CT) apparatus, and the processing circuitry reconstructs, from the raw data, the medical image corresponding to the specified time.

* * * * *